(12) United States Patent
Kim

(10) Patent No.: US 11,317,866 B2
(45) Date of Patent: May 3, 2022

(54) OPTICAL SENSOR, OPTICAL SENSOR ARRAY AND APPARATUS AND METHOD FOR MEASURING BIO-SIGNAL

(71) Applicant: SAMSUNG ELECTRONICS CO., LTD., Suwon-si (KR)

(72) Inventor: Dong Ho Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 241 days.

(21) Appl. No.: 16/521,997

(22) Filed: Jul. 25, 2019

(65) Prior Publication Data

US 2020/0029904 A1 Jan. 30, 2020

(30) Foreign Application Priority Data

Jul. 27, 2018 (KR) .................. 10-2018-0088099

(51) Int. Cl.
*A61B 5/1455* (2006.01)
*A61B 5/00* (2006.01)
*A61B 5/145* (2006.01)

(52) U.S. Cl.
CPC .......... *A61B 5/6844* (2013.01); *A61B 5/1455* (2013.01); *A61B 5/14532* (2013.01); *A61B 5/14546* (2013.01); *A61B 2562/046* (2013.01)

(58) Field of Classification Search
CPC .............. A61B 5/6844; A61B 5/14532; A61B 5/14546; A61B 5/1455; A61B 2562/046
See application file for complete search history.

(56) References Cited

U.S. PATENT DOCUMENTS

| 8,107,776 | B2 | 1/2012 | Wang et al. | |
|---|---|---|---|---|
| 8,437,584 | B2 | 5/2013 | Matsuoka et al. | |
| 8,592,881 | B2 | 11/2013 | Lee et al. | |
| 8,675,272 | B2 | 3/2014 | Cho et al. | |
| 9,592,007 | B2 * | 3/2017 | Nuovo ................ | A61B 5/0059 |
| 2014/0107493 | A1 * | 4/2014 | Yuen .................... | A61B 5/6898 600/473 |
| 2015/0164353 | A1 | 6/2015 | Messerschmidt et al. | |
| 2015/0201841 | A1 | 7/2015 | Ishikawa et al. | |
| 2016/0161331 | A1 * | 6/2016 | Liu ..................... | A61B 5/1455 250/552 |
| 2016/0206206 | A1 | 7/2016 | Avila et al. | |
| 2017/0215779 | A1 | 8/2017 | Koide et al. | |
| 2017/0340257 | A1 | 11/2017 | Aung et al. | |

(Continued)

FOREIGN PATENT DOCUMENTS

| EP | 3318854 A1 | 5/2018 |
|---|---|---|
| JP | 2013009710 A * | 1/2013 |

(Continued)

OTHER PUBLICATIONS

Communication dated Nov. 14, 2019 by the European Patent Office in counterpart European Patent Application No. 19188556.5.

*Primary Examiner* — Eric F Winakur
(74) *Attorney, Agent, or Firm* — Sughrue Mion, PLLC

(57) ABSTRACT

An optical sensor, an optical sensor array, and an apparatus and method for measuring a bio-signal are provided. The optical sensor includes a photodetector, and a light source disposed on the photodetector. The optical sensor is configured to operate the light source in a light source mode, and operate the photodetector in a photodetector mode, based on a control signal.

25 Claims, 13 Drawing Sheets

(56) References Cited

U.S. PATENT DOCUMENTS

| | | |
|---|---|---|
| 2018/0128680 A1 | 5/2018 | Kim |
| 2018/0146855 A1 | 5/2018 | Anikanov et al. |
| 2018/0168508 A1* | 6/2018 | Biel ........................ A61B 5/282 |
| 2018/0177439 A1 | 6/2018 | Sia et al. |

FOREIGN PATENT DOCUMENTS

| | | |
|---|---|---|
| KR | 10-0765465 B1 | 10/2007 |
| KR | 10-2013-0000263 A | 1/2013 |
| KR | 10-2013-0046164 A | 5/2013 |
| KR | 10-2017-0029372 A | 3/2017 |
| KR | 10-2017-0037344 A | 4/2017 |
| KR | 10-2017-0080108 A | 7/2017 |

\* cited by examiner

OPTICAL SENSOR, OPTICAL SENSOR ARRAY AND APPARATUS AND METHOD FOR MEASURING BIO-SIGNAL

CROSS-REFERENCE TO RELATED APPLICATION

This application claims priority from Korean Patent Application No. 10-2018-0088099, filed on Jul. 27, 2018, in the Korean Intellectual Property Office, the disclosure of which is incorporated herein by reference in its entirety.

BACKGROUND

1. Field

Apparatuses and methods consistent with embodiments relate to non-invasively measuring a bio-signal.

2. Description of Related Art

Diabetes mellitus is a chronic disease that is difficult to treat and causes various complications, and hence a blood sugar level may be checked regularly to prevent any complications. When insulin is administered, blood sugar may be checked to prevent hypoglycemia and control the insulin dosage. Generally, measuring blood sugar includes an invasive method. The method of measuring blood sugar in an invasive manner has high reliability of measurement, but the use of injection may cause pain during blood sampling, inconvenience, and a risk of infection. Recently, a method of non-invasive measurement of blood sugar using an optical sensor, without directly collecting blood, has been studied.

SUMMARY

According to embodiments, there is provided an optical sensor including a photodetector, and a light source disposed on the photodetector. The optical sensor is configured to operate the light source in a light source mode, and operate the photodetector in a photodetector mode, based on a control signal.

The optical sensor may further include a photodetector electrode on which the photodetector is disposed, a common electrode interposed between the photodetector and the light source, and a light source electrode disposed on the light source.

The common electrode may be configured to reflect light that is emitted from a light emitting layer of the light source toward the photodetector.

The common electrode may include one among conductive materials including Al, Ag, Pt, Pd, Au, Rh, Al alloy, Ag alloy, Pt alloy, Pd alloy, Au alloy, and Rh alloy.

The optical sensor may further include a power source configured to apply power to the light source through the light source electrode and the common electrode, in the light source mode, and apply power to the photodetector through the photodetector electrode and the common electrode, in the photodetector mode.

The optical sensor may further include a mode controller configured to connect the light source electrode and the common electrode to the power source, in the light source mode, and connect the photodetector electrode and the common electrode to the power source, in the photodetector mode.

The control signal may include mode selection information indicating one among the light source mode and the photodetector mode that is selected, and mode duration information of the selected one among the light source mode and the photodetector mode.

The control signal may be pulse-shaped.

According to embodiments, there is provided an optical sensor array including a plurality of optical sensors. Each of the plurality of optical sensors includes a photodetector; and a light source disposed on the photodetector. Each of the plurality of optical sensors is configured to operate the light source in a light source mode, and operate the photodetector in a photodetector mode, based on a control signal.

The optical sensor array may be a square array or a hexagonal array.

According to embodiments, there is provided an apparatus for measuring a bio-signal, the apparatus including an optical sensor array including a plurality of optical sensors. Each of the plurality of optical sensors includes a photodetector, and a light source disposed on the photodetector. Each of the plurality of optical sensors is configured to operate the light source in a light source mode, and operate the photodetector in a photodetector mode, based on a control signal. The apparatus further includes a processor configured to control one among the plurality of optical sensors to operate in the light source mode, and control at least two among the plurality of optical sensors to operate in the photodetector mode, to acquire optical absorption information of optical pathlengths with respect to an object of interest.

The processor may be further configured to control the one among the plurality of optical sensors to emit first light to the object of interest, and control the at least two among the plurality of optical sensors to receive second light that is reflected or scattered from the object of interest to which the first light is emitted, to acquire the optical absorption information of the optical pathlengths.

The processor may be further configured to estimate bio-information of the object of interest, based on the acquired optical absorption information of the optical pathlengths.

The bio-information may include any one or any combination of triglyceride, blood glucose, cholesterol, protein, and uric acid.

The processor may be further configured to determine a contact state between the optical sensor array and the object of interest, using a pair of the plurality of optical sensors.

The processor may be further configured to control a first one of the pair of the plurality of optical sensors to operate in the light source mode, and control a second one of the pair of the plurality of optical sensors to operate in the photodetector mode, to acquire first optical absorption information, control the second one of the pair of the plurality of optical sensors to operate in the light source mode, and control the first one of the pair of the plurality of optical sensors to operate in the photodetector mode, to acquire second optical absorption information, and compare the acquired first optical absorption information and the acquired second optical absorption information, to determine the contact state between the optical sensor array and the object of interest.

The processor may be further configured to, based on the contact state between the optical sensor array and the object of interest being determined to be poor, control to provide a warning message to a user.

Each of the plurality of optical sensors may further include a photodetector electrode on which the photodetector is disposed, a common electrode interposed between the photodetector and the light source, and a light source electrode disposed on the light source.

The common electrode may be configured to reflect light that is emitted from a light emitting layer of the light source toward the photodetector.

The common electrode may include one among conductive materials including Al, Ag, Pt, Pd, Au, Rh, Al alloy, Ag alloy, Pt alloy, Pd alloy, Au alloy, and Rh alloy.

Each of the plurality of optical sensors further may include a mode controller configured to connect the light source electrode and the common electrode to a power source, in the light source mode, and connect the photodetector electrode and the common electrode to the power source, in the photodetector mode.

The optical sensor array may be a square array or a hexagonal array.

According to embodiments, there is provided a method of measuring a bio-signal, using an optical sensor array that includes a plurality optical sensors, each of the plurality of optical sensors including a photodetector and a light source disposed on the photodetector, each of the plurality of optical sensors operating the light source in a light source mode and operating the photodetector in a photodetector mode, based on a control signal. The method includes controlling one among the plurality of optical sensors to operate in the light source mode so that the one among the plurality of optical sensors emits first light to an object of interest, and controlling at least two among the plurality of optical sensors to operate in the photodetector mode so that the at least two among the plurality of optical sensors receive second light that is reflected or scattered from the object of interest to which the first light is emitted, to acquire optical absorption information of optical pathlengths with respect to the object of interest.

The method may further include estimating bio-information of the object of interest, based on the acquired optical absorption information of the optical pathlengths.

The bio-information may include any one or any combination of triglyceride, blood glucose, cholesterol, protein, and uric acid.

The method may further include determining a contact state between the optical sensor array and the object of interest, using a pair of the plurality of optical sensors.

The method may further include controlling a first one of the pair of the plurality of optical sensors to operate in the light source mode, and controlling a second one of the pair of the plurality of optical sensors to operate in the photodetector mode, to acquire first optical absorption information, and controlling the second one of the pair of the plurality of optical sensors to operate in the light source mode, and controlling the first one of the pair of the plurality of optical sensors to operate in the photodetector mode, to acquire second optical absorption information. The determining the contact state between the optical sensor array and the object of interest may include comparing the acquired first optical absorption information and the acquired second optical absorption information.

The method may further include, based on the contact state between the optical sensor array and the object of interest being determined to be poor, controlling to provide a warning message to a user.

According to embodiments, there is provided a mobile device including an optical sensor array including a plurality of optical sensors; and a processor configured to control one among the plurality of optical sensors to emit first light to an object of interest, and control at least two among the plurality of optical sensors to receive second light that is reflected or scattered from the object of interest to which the first light is emitted, to acquire optical absorption information of optical pathlengths with respect to the object of interest.

The processor may be further configured to determine a contact state between the optical sensor array and the object of interest, based on the contact state between the optical sensor array and the object of interest being determined to be poor, control to provide a warning message to a user, and based on the contact state between the optical sensor array and the object of interest being determined to be good, control the one among the plurality of optical sensors to emit the first light to the object of interest, and control the at least two among the plurality of optical sensors to receive the second light that is reflected or scattered from the object of interest to which the first light is emitted, to acquire the optical absorption information of the optical pathlengths.

DETAILED DESCRIPTION

Figure 1:
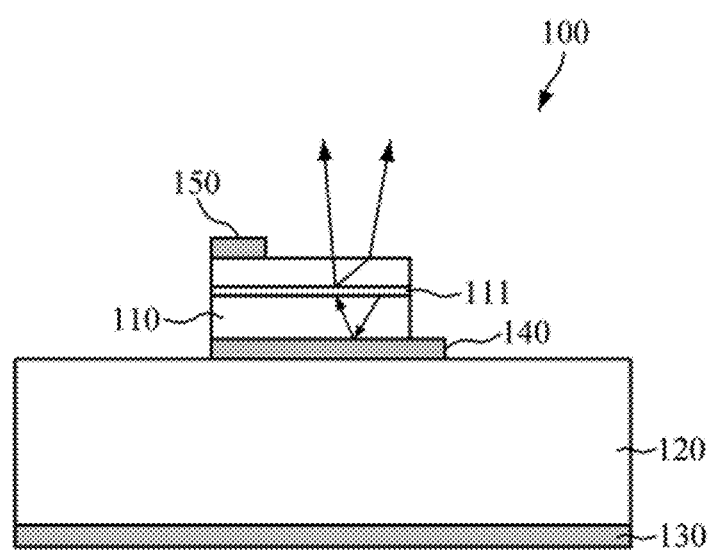
FIG. 1 is a cross-sectional view of an optical sensor according to embodiments.

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail. Throughout the drawings and the detailed description, unless otherwise described, the same drawing reference numerals will be understood to refer to the same elements, features, and structures. The relative size and depiction of these elements may be exaggerated for clarity, illustration, and convenience.

In some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiments and meanings may vary depending on, for example, a user or operator's intentions or customs. Therefore, in the following embodiments, when terms are defined, the meanings of terms may be interpreted based on definitions, and otherwise, may be interpreted based on general meanings recognized by those skilled in the art.

It will be understood that, although the terms "first," "second," etc. may be used herein to describe various elements, these elements may not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising" will be understood to imply the inclusion of stated elements but not the exclusion of any other elements. Terms such as "unit" and "module" denote units that process at least one function or operation, and they may be implemented by using hardware, software, or a combination of hardware and software.

According to embodiments, optical absorption information of various optical pathlengths with respect to an object of interest is obtained using an optical sensor formed by stacking a light source and a photodetector, thereby making it possible to reduce the size of a device and improve accuracy in estimating biological components.

FIG. 1 is a cross-sectional view of an optical sensor according to embodiments.

Referring to FIG. 1, an optical sensor 100 may include a light source 110 and a photodetector 120. The light source 110 and the photodetector 120 may be formed in a stacked structure. According to embodiments, the light source 110 may be stacked on the photodetector 120.

The light source 110 may emit light to an object of interest. According to embodiments, the light source 110 may emit visible rays or infrared rays to the object of interest. However, a wavelength of light emitted from the light source may vary depending on the purpose of measurement or the type of component to be analyzed. In addition, the light source is not necessarily configured with a single light emitting body and may be configured with a set of a plurality of light emitting bodies. According to embodiments, the light source may be formed as a light emitting diode (LED), a laser diode, or a phosphor, but is not limited thereto.

The photodetector 120 may receive light reflected or scattered from the object of interest and measure intensity of the received light. According to embodiments, the photodetector 120 may include a photodiode, a photo transistor, or a charge-coupled device (CCD), but is not limited thereto.

The optical sensor 100 may operate in a light source mode or in a photodetector mode according a predetermined control signal. The light source mode is a mode in which the optical sensor 100 serves as a light source, and the photodetector mode is a mode in which the optical sensor 100 serves as a photodetector. In the light source mode, only the light source 110 may operate and the photodetector 120 may not operate. In the photodetector mode, only the photodetector 120 may operate and the light source 110 may not operate.

The predetermined control signal is a pulse-shaped signal, which may include mode selection information and mode duration information. That is, the light source 110 and the photodetector 120 may be pulse-driven according to the predetermined control signal.

The optical sensor 100 may include a photodetector electrode 130, a common electrode 140, and a light source electrode 150.

The photodetector electrode 130 may be an electrode that applies power to the photodetector 120 for operation of the photodetector 120. The photodetector electrode 130 may be formed on a bottom of the photodetector 120.

The common electrode 140 may be an electrode shared between the light source 110 and the photodetector 102 and may be an electrode that applies power to the light source 110 or the photodetector 120 for operation of the light source 110 or the photodetector 120. The common electrode 140 may be interposed between the light source 110 and the photodetector 120. According to embodiments, the common electrode 140 may be formed of a conductive material, such as Al, Ag, Pt, Pd, Au, Rh, Al alloy, Ag alloy, Pt alloy, Pd alloy, Au alloy, or Rh alloy to reflect light emitted from a light emitting layer (e.g., a multi quantum well (MQW) 111) of the light source 110 toward the photodetector 120.

The light source electrode 150 may be an electrode that applies power to the light source 110 for operation of the light source 110. The light source electrode 150 may be formed on an upper portion of the light source 110. According to embodiments, the light source electrode 150 may be formed of a transparent conductive material, such as indium tin oxide (ITO) or indium zinc oxide (IZO) that does not affect the propagation of light.

Figure 2:
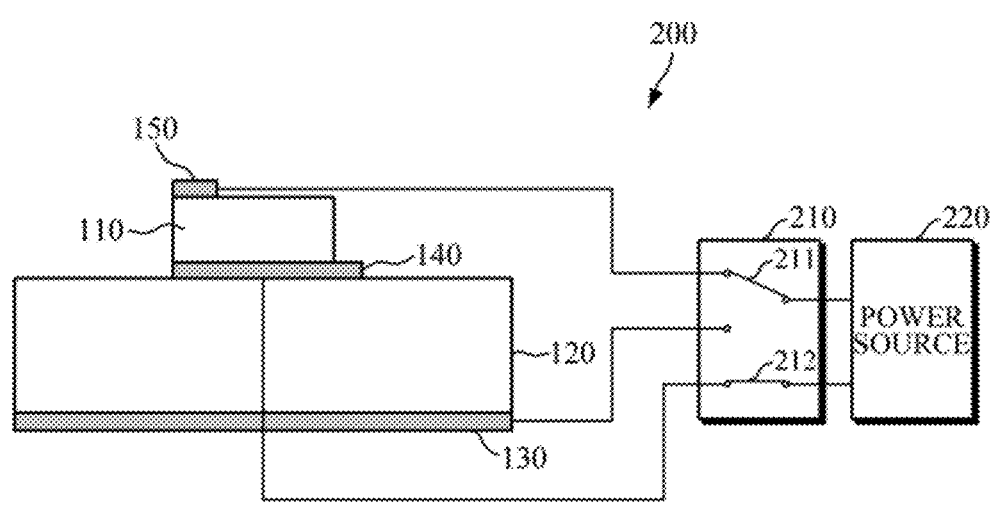
FIG. 2 is a diagram illustrating an optical sensor according to embodiments.

FIG. 2 is a diagram illustrating an optical sensor according to embodiments.

Referring to FIG. 2, an optical sensor 200 may include a light source 110, a photodetector 120, three electrodes 130, 140, and 150, a mode controller 210, and a power source 220. Here, the light source 110, the photodetector 120, and the three electrodes 130, 140, and 150 are substantially the same as those described above with reference to FIG. 1, and thus detailed descriptions thereof will not be reiterated.

The mode controller 210 may control an operation mode of the optical sensor 200 in response to a predetermined control signal. To this end, the mode controller 210 may include two switches 211 and 212.

According to embodiments, in a light source mode, the mode controller 210 may connect a light source electrode 150 and the power source 220 using the first switch 211 and connect a common electrode 140 and the power source 220 using the second switch 212. In addition, in a photodetector mode, the mode controller 210 may connect a photodetector electrode 130 and the power source 220 using the first switch 211 and connect the common electrode 140 and the power source 220 using the second switch 212.

The power source 220 may apply power to the light source 110 or the photodetector 120. For example, the power source 220 may apply power to the light source 110 using the light source electrode 150 and the common electrode 140 in the light source mode, and may apply power to the photodetector 120 using the photodetector electrode 130 and the common electrode 140 in the photodetector mode.

In FIG. 2, the optical sensor 200 is illustrated as including the power source 220, but the embodiments are not limited thereto, such that the power source 220 may be formed outside of the optical sensor 200.

Hereinafter, an example in which a plurality of optical sensors is gathered to form an optical sensor array will be described.

Figure 3A:
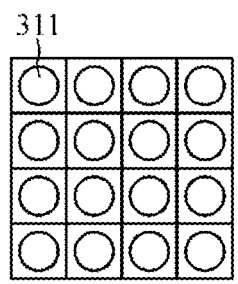
FIG. 3A is a diagram illustrating an arrangement structure of an optical sensor array according to embodiments.
Figure 3B:
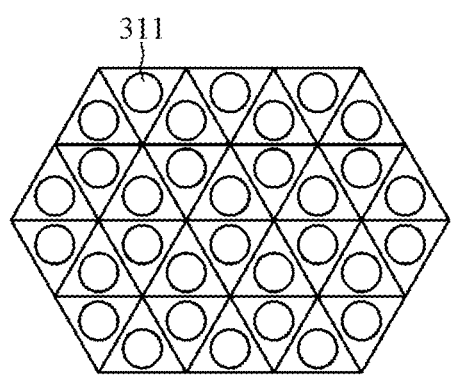
FIG. 3B is a diagram illustrating an arrangement structure of an optical sensor array according to embodiments.

FIG. 3A is a diagram illustrating an arrangement structure of an optical sensor array according to embodiments, and FIG. 3B is a diagram illustrating an arrangement structure of an optical sensor array according to embodiments. Here, an optical sensor 311 may be the optical sensor 100 of FIG. 1 or the optical sensor 200 of FIG. 2.

The optical sensor array includes a plurality of optical sensors 311 and may be implemented as a square array, as shown in FIG. 3A, or may be implemented as a hexagonal array, as shown in FIG. 3B. However, the array structures shown in FIGS. 3A and 3B are embodiments and the structure of the optical sensor array is not limited thereto.

The optical sensor array may be mounted in an electronic device. In this case, the electronic device may include a mobile phone, a smartphone, a tablet computer, a notebook computer, a personal digital assistant (PDA), a portable multimedia player (PMP), a navigation system, an MP3 player, a digital camera, a wearable device, and the like. The wearable device may include wearable devices of various types, such as a wristwatch type, a wrist band type, a ring type, a belt type, a necklace type, an ankle band type, a thigh band type, a forearm band type, and the like. However, the electronic device and the wearable device are not limited to the above-describe examples.

Figure 4:
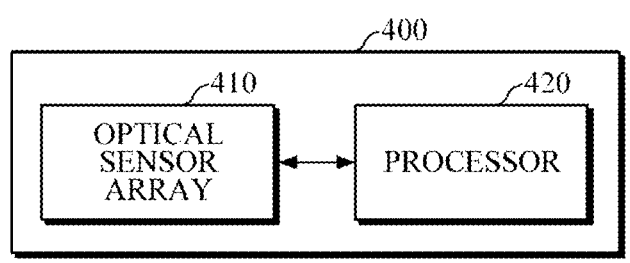
FIG. 4 is a block diagram of an apparatus for measuring a bio-signal according to embodiments.
Figure 5:
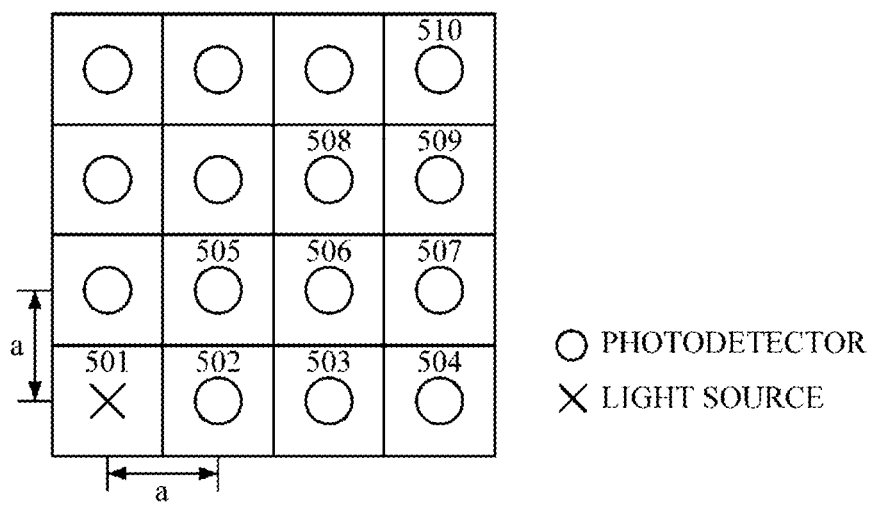
FIG. 5 is a diagram for describing a method of acquiring optical absorption information of various optical pathlengths, according to embodiments.

FIG. 4 is a block diagram illustrating an apparatus for measuring a bio-signal according to embodiments, and FIG. 5 is a diagram for describing a method of acquiring optical absorption information of various optical pathlengths, according to embodiments.

An apparatus 400 for measuring a bio-signal of FIG. 4 is an apparatus for acquiring optical absorption information of various optical pathlengths with respect to an object of interest, and estimating bio-information of the object of interest on the basis of the acquired optical absorption information of various optical pathlengths, which may be mounted in an electronic device. Here, the electronic device may include a mobile phone, a smartphone, a tablet computer, a notebook computer, a PDA, a PMP, a navigation system, an MP3 player, a digital camera, a wearable device, and the like. The wearable device may include wearable devices of various types, such as a wristwatch type, a wrist band type, a ring type, a belt type, a necklace type, an ankle band type, a thigh band type, a forearm band type, and the like. However, the electronic device and the wearable device are not limited to the above-describe examples.

Referring to FIG. 4, the apparatus 400 for measuring a bio-signal may include an optical sensor array 410 and a processor 420. The optical sensor array 410 is the substantially the same as the optical sensor array described above with reference to FIGS. 1 to 3B, and thus a detailed description thereof will not be reiterated.

The processor 420 may operate an overall operation of the apparatus 400 for measuring a bio-signal.

The processor 420 may use the optical sensor array 410 to determine a contact state between the object of interest and the optical sensor array 410.

The processor 420 may select two optical sensors to be used in determining the contact state from the optical sensor array 410 and may use the two selected optical sensors to determine the contact state between the object of interest and the optical sensor array 410. For example, the processor 420 may acquire first optical absorption information by operating one (hereinafter referred to as a "first optical sensor") of the two selected optical sensors in a light source mode and operating the other (hereinafter referred to as a "second optical sensor") of the two selected optical sensors in a photodetector mode. Also, the processor 420 may acquire second optical absorption information by operating the second optical sensor in the light source mode and operating the first optical sensor in the photodetector mode. In addition, the processor 420 may compare the first optical absorption information and the second optical absorption information. When a difference between the first optical absorption information and the second optical absorption information is less than or equal to a predetermined threshold, the processor 420 may determine that the object of interest is in good contact with the optical sensor array 410, and when the difference between the first optical absorption information and the second optical absorption information is greater than the predetermined threshold, the processor 420 may determine that the object of interest is in poor contact with the optical sensor array 410.

When the processor 420 determines that the optical sensor array 410 is in poor contact with the object of interest, the processor 420 may generate a warning message and provide the generated warning message to a user through an output interface. In this case, the output interface may include an audible output interface, such as a speaker, a visual output interface, such as a display, and a tactile output interface, such as a vibrator.

The processor 420 may use the optical sensor array 410 to acquire optical absorption information of various optical pathlengths with respect to the object of interest.

The processor 420 may select at least one optical sensor (hereinafter referred to as a "light source optical sensor") to be used as a light source from the optical sensor array 410 and select at least one other sensor (hereinafter referred to as a "photodetector optical sensor") to be used as a photodetector from the optical sensor array 410.

The processor 420 may generate a control signal and control the optical sensor array 410 so that the selected light source optical sensor operates in a light source mode and the selected photodetector optical sensor operates in a photodetector mode.

The processor 420 may operate the light source optical sensor in the light source mode to emit light to the object of interest and may operate the photodetector optical sensor in the photodetector mode to measure intensity of light reflected or scattered from the object irradiated by the light source optical sensor, thereby acquiring the optical absorption information of various optical pathlengths with respect to the object of interest.

For example, referring to FIG. 5, the processor 420 may select an optical sensor 501 as a light source optical sensor and select optical sensors 502 to 510 as photodetector optical sensors. The processor 420 may operate the optical sensor 501 in the light source mode to emit light to the object of interest and operate the optical sensors 502 to 510 in the photodetector mode to receive light reflected or scattered from the object of interest. At this time, the light received by the optical sensor 502 may include optical absorption information of a pathlength of a, the light received by the optical sensor 503 may include optical absorption information of a pathlength of $2a$, and the light received by the optical sensor 504 may include optical absorption information of a pathlength of $3a$. Further, the light received by the optical sensor 505 may include optical absorption information of a pathlength of $\sqrt{2}a$, the light received by the optical sensor 506 may include optical absorption information of a pathlength of $\sqrt{5}a$, and the light received by the optical sensor 507 may include optical absorption information of a pathlength of $\sqrt{10}a$. Further, the light received by the optical sensor 508 may include optical absorption information of a pathlength of $2\sqrt{2}a$, the light received by the optical sensor 509 may include optical absorption information of a pathlength of $\sqrt{13}a$, and the light received by the optical sensor 510 may include optical absorption information of a pathlength of 3 $\sqrt{2}a$. That is, the processor 420 may acquire pieces of optical absorption information of various pathlengths (a, 2a, 3a, $\sqrt{2}a$, $\sqrt{5}a$, $\sqrt{10}a$, $2\sqrt{2}a$, and $\sqrt{13}a$).

The processor 420 may estimate bio-information of the object of interest on the basis of the optical absorption information of various optical pathlengths with respect to the object of interest. In this case, the bio-information may include triglyceride, blood glucose, cholesterol, protein, uric acid, etc. According to embodiments, the processor 420 may estimate the bio-information of the object of interest using the Beer Lambert's Law.

Figure 6:
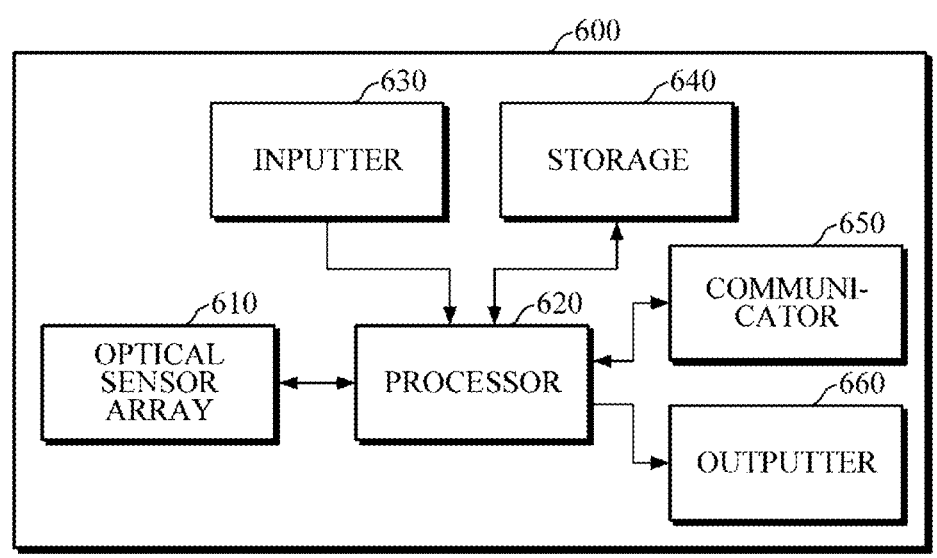
FIG. 6 is a block diagram of an apparatus for measuring a bio-signal according to embodiments.

FIG. 6 is a block diagram of an apparatus for measuring a bio-signal according to embodiments.

An apparatus 600 for measuring a bio-signal shown in FIG. 6 may be mounted in an electronic device. Here, the electronic device may include a mobile phone, a smartphone, a tablet computer, a notebook computer, a PDA, a PMP, a navigation system, an MP3 player, a digital camera, a wearable device, and the like. The wearable device may include wearable devices of various types, such as a wristwatch type, a wrist band type, a ring type, a belt type, a necklace type, an ankle band type, a thigh band type, a forearm band type, and the like. However, the electronic device and the wearable device are not limited to the above-describe examples.

Referring to FIG. 6, the apparatus 600 for measuring a bio-signal may include an optical sensor array 610, a processor 620, an inputter 630 or an input interface, a storage 640, a communicator 650 or a communication interface, and an outputter 660 or an output interface. Here, the optical sensor array 610 and the processor 620 are substantially the same as the optical sensor array 410 and the processor 420 described above with reference to FIGS. 1 to 5, respectively, and thus detailed descriptions thereof will not be reiterated.

The inputter 630 may receive various operation signals from a user. According to embodiments, the inputter 630 may include a key pad, a dome switch, a touch pad (resistive/capacitive), a jog wheel, a jog switch, a hardware button, and the like. When a touch pad has a layered structure with a display, this structure may be referred to as a touch screen.

Programs or instructions for operation of the apparatus 600 for measuring a bio-signal may be stored in the storage 640, and data input to and output from the apparatus 600 may also be stored in the storage 640. In addition, pieces of optical absorption information of various optical pathlengths with respect to an object of interest measured through the optical sensor array 610 and biological component information estimated therefrom may be stored in the storage 640.

The storage 640 may include at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk. In addition, the apparatus 600 for measuring a bio-signal may operate an external storage medium, such as a web storage that performs the storage function of the storage 640 on the Internet.

The communicator 650 may communicate with an external device. For example, the communicator 650 may transmit data input from the user through the inputter 630, the optical absorption information of various optical pathlengths with respect to the object of interest measured through the optical sensor array 610, biological component information estimated using the optical absorption information of various optical pathlengths, and the like to the external device. Further, the communicator 650 may receive a variety of data for measuring optical absorption information of various optical pathlengths and estimate a biological component from the external device.

In this case, the external device may be medical equipment that uses the data input from the user through the inputter 630, the optical absorption information of various optical pathlengths with respect to the object of interest measured through the optical sensor array 610, and the biological component information estimated using the optical absorption information of various optical pathlengths, or a printer or a display device to output a result. In addition, the external device may be a digital TV, a desktop computer, a mobile phone, a smartphone, a tablet computer, a PDA, a PMP, a navigation system, an MP3 player, a digital camera, a wearable device, or the like, but is not limited thereto.

The communicator 650 may communicate with the external device using, for example, Bluetooth, Bluetooth low energy (BLE) communication, near-field communication (NFC), wireless local access network (WLAN) communication, ZigBee communication, infrared data association (IrDA) communication, Wi-Fi direct (WFD) communication, ultra-wideband (UWB) communication, Ant+communication, Wi-Fi communication, radio frequency identification (RFID) communication, 3rd generation (3G) communication, 4G communication, and the 5G communication. However, these are examples and the embodiments are not limited thereto.

The outputter 660 may output the data input from the user through the inputter 630, the optical absorption information of various optical pathlengths with respect to the object of interest measured through the optical sensor array 610, biological component information estimated using the optical absorption information of various optical pathlengths, a warning message due to poor contact between the object of interest and the optical sensor array 610, and the like. According to embodiments, the outputter 660 may output the data input from the user through the inputter 630, the optical absorption information of various optical pathlengths with respect to the object of interest measured through the optical sensor array 610, the biological component information estimated using the optical absorption information of various optical pathlengths, the warning message due to poor contact between the object of interest and the optical sensor array 610, and the like, using any one or any combination of an audible method, a visual method, and a tactile method. To this end, the outputter 660 may include a display, a speaker, a vibrator, etc.

Figure 7:
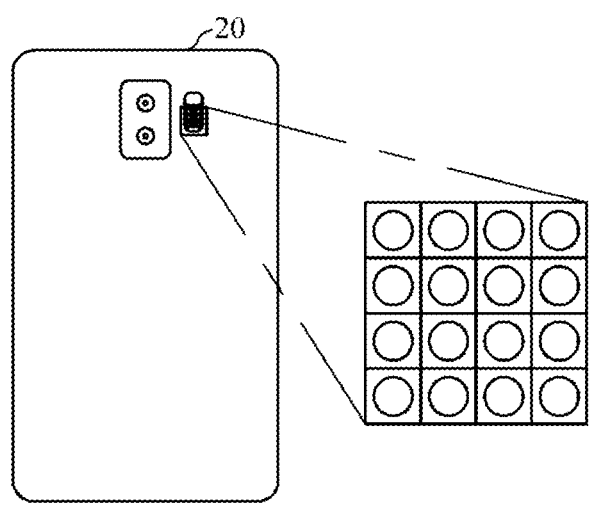
FIG. 7 is a diagram illustrating an example to which an optical sensor array according to embodiments is applied.
Figure 8:
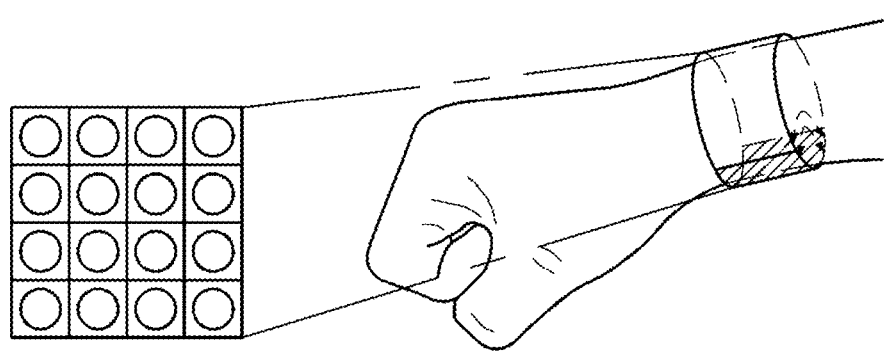
FIG. 8 is a diagram illustrating another example to which an optical sensor array according to embodiments is applied.
Figure 9:
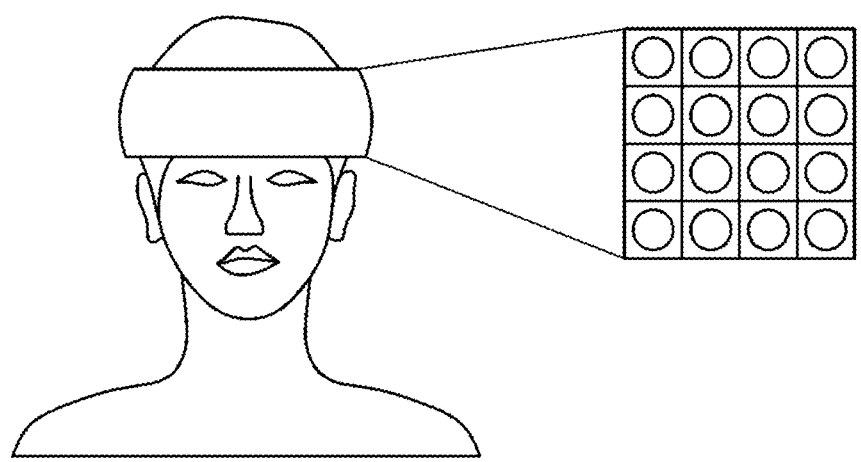
FIG. 9 is a diagram illustrating still another example to which an optical sensor array according to embodiments is applied.

FIG. 7 is a diagram illustrating an example to which an optical sensor array according to embodiments is applied, FIG. 8 is a diagram illustrating another example to which an optical sensor array according to embodiments is applied, and FIG. 9 is a diagram illustrating still another example to which an optical sensor array according to embodiments is applied.

An optical sensor array according to embodiments may be applied to a rear surface of a mobile phone or a smartphone 20 as shown in FIG. 7, or may be applied to a wrist-type wearable device as shown in FIG. 8. In addition, the optical sensor array may be applied to a wearable brain-imaging device, as shown in FIG. 9.

Figure 10:
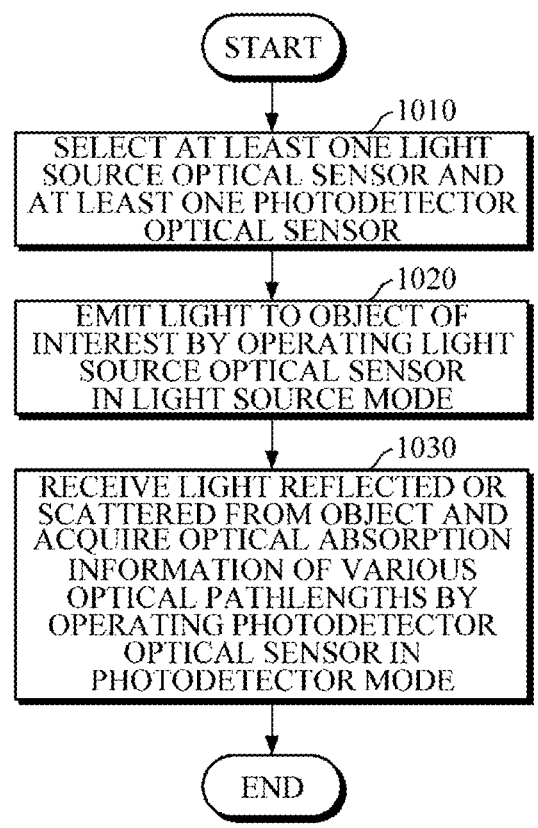
FIG. 10 is a flowchart illustrating a method of measuring a bio-signal, according to embodiments.

FIG. 10 is a flowchart illustrating a method of measuring a bio-signal, according to embodiments. The method shown in FIG. 10 may correspond to a method performed by the apparatus 400 of FIG. 4 to measure a bio-signal.

Referring to FIG. 10, the apparatus for measuring a bio-signal may select at least one light source optical sensor from an optical sensor array and select at least one photodetector optical sensor from the optical sensor array, in operation 1010. For example, in the example of FIG. 5, the apparatus for measuring a bio-signal may select the optical sensor 501 as a light source optical sensor and select the optical sensors 502 to 510 as photodetector optical sensors.

The apparatus may operate the light source optical sensor in a light source mode to emit light to an object of interest, in operation 1020. For example, in the example of FIG. 5, the apparatus may use the optical sensor 501 to emit light to the object of interest.

The apparatus for measuring a bio-signal may operate the photodetector optical sensors in a photodetector mode to receive light reflected or scattered from the object of interest and acquire optical absorption information of various optical pathlengths, in operation 1030. For example, in the example of FIG. 5, the apparatus may receive light reflected or scattered from the object of interest using the optical sensors 502 to 510, thereby acquiring pieces of optical absorption information of various optical pathlengths of a, 2a, 3a, $\sqrt{2}a$, $\sqrt{5}a$, $\sqrt{10}a$, $2\sqrt{2}a$, and $\sqrt{13}a$.

Figure 11:
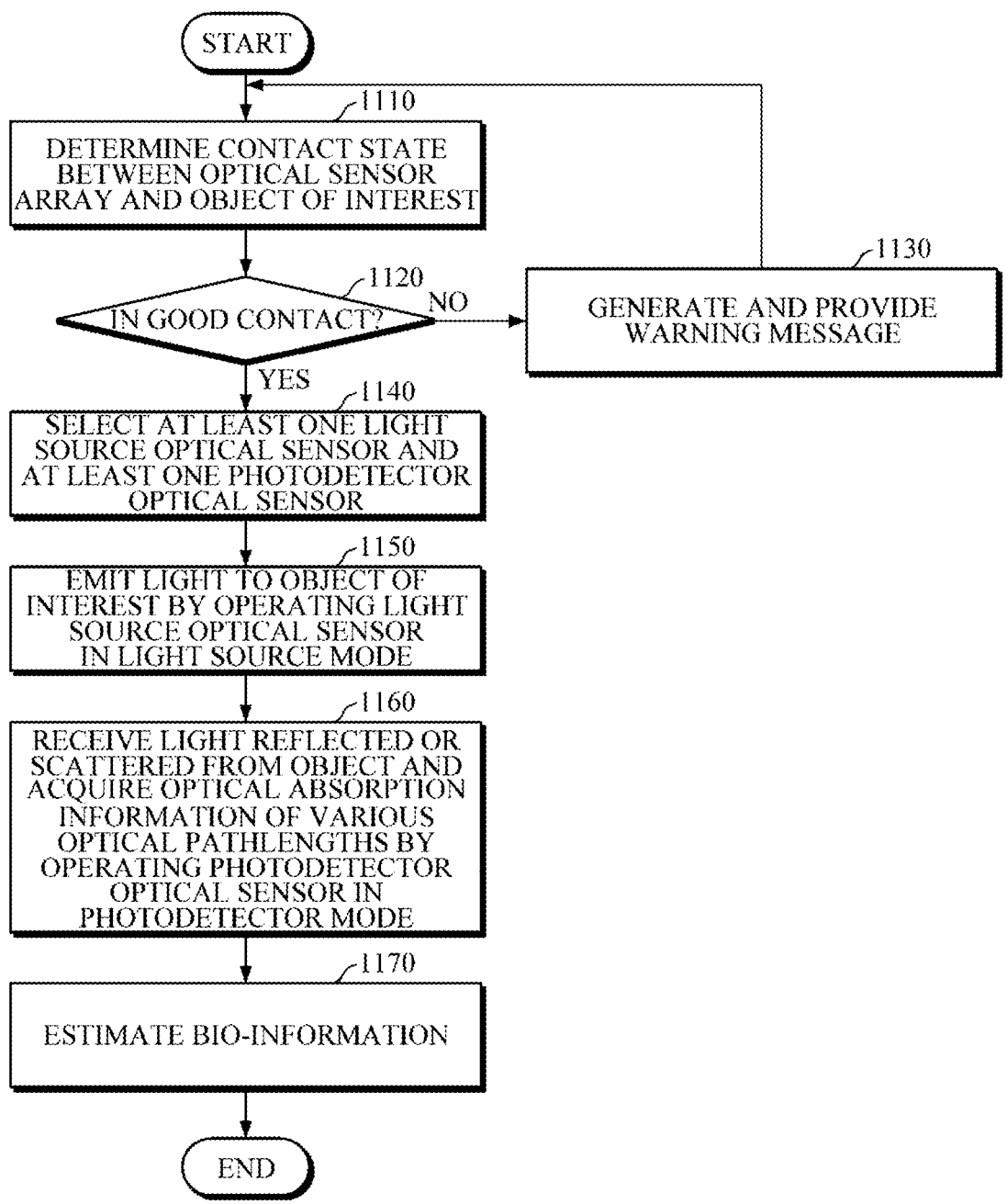
FIG. 11 is a flowchart illustrating a method of measuring a bio-signal, according to embodiments.

FIG. 11 is a flowchart illustrating a method of measuring a bio-signal, according to embodiments. The method shown in FIG. 11 may correspond to a method performed by the apparatus 400 of FIG. 4 to measure a bio-signal.

Referring to FIG. 11, in operation 1110, the apparatus for measuring a bio-signal may determine a contact state between an optical sensor array and an object of interest.

In operation 1120, the apparatus may determine whether the optical sensor array is in good contact with the object of interest.

In operation 1130, when it is determined that the optical sensor array is in poor contact with the object of interest, the apparatus may generate a warning message and provide it to a user.

In operation 1140, when it is determined that the optical sensor array is in good contact with the object of interest, the apparatus for measuring a bio-signal may select at least one light source optical sensor from the optical sensor array and select at least one photodetector optical sensor from the optical sensor array.

In operation 1150, the apparatus for measuring a bio-signal may operate the selected light source optical sensors in a light source mode to emit light to the object of interest.

In operation 1160, the apparatus for measuring a bio-signal may operate the selected photodetector optical sensors in a photodetector mode to receive light reflected or scattered from the object of interest, thereby acquiring optical absorption information of various optical pathlengths.

In operation 1170, the apparatus for measuring a bio-signal may estimate bio-information of the object of interest on the basis of the optical absorption information of various optical pathlengths with respect to the object of interest. Here, the bio-information may include triglyceride, blood glucose, cholesterol, protein, uric acid, etc. For example, the apparatus for measuring a bio-signal may estimate the bio-information of the object of interest using the Beer-Lambert's law.

Figure 12:
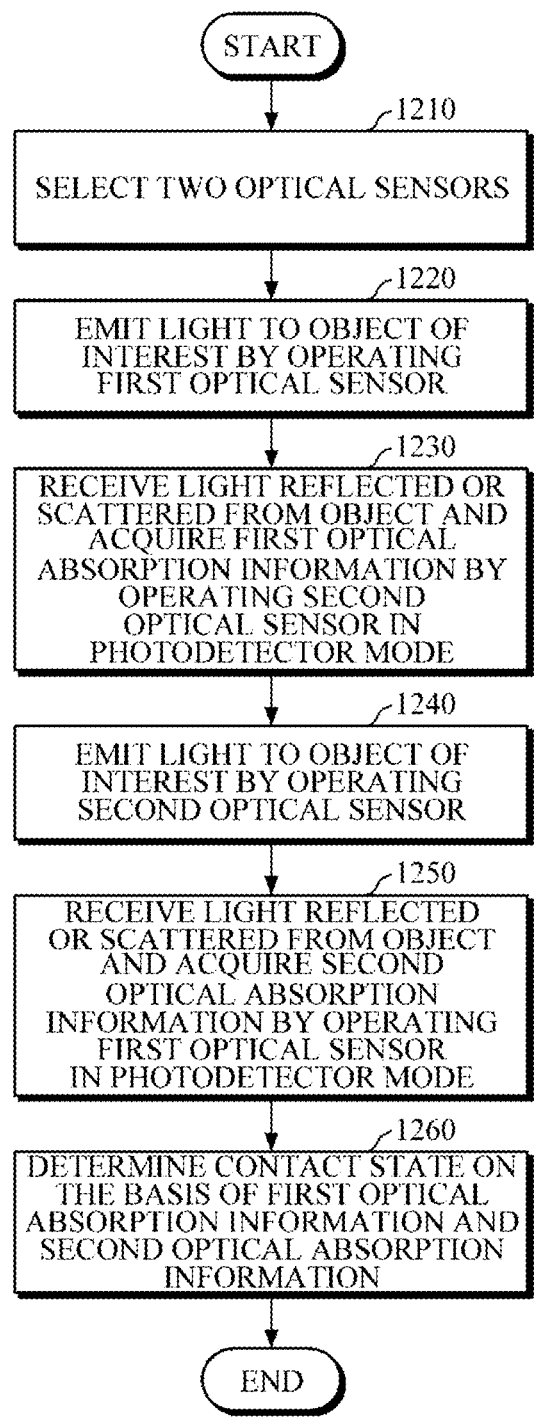
FIG. 12 is a flowchart illustrating a method of determining a contact state between an object of interest and an optical sensor array, according to embodiments.

FIG. 12 is a flowchart illustrating a method of determining a contact state between an object of interest and an optical sensor array, according to embodiments. The method of determining a contact state may be an embodiment of operation 1110 described in FIG. 11.

Referring to FIG. 12, in operation 1210, an apparatus for measuring a bio-signal may select two optical sensors to be used in determining a contact state from an optical sensor array.

In operation 1220, the apparatus for measuring a bio-signal may operate a first optical sensor of the two selected optical sensors in a light source mode to emit light to the object of interest.

In operation 1230, the apparatus for measuring a bio-signal may operate a second optical sensor of the two selected optical sensors in a photodetector mode to receive light reflected or scattered from the object of interest and acquire first optical absorption information.

In operation 1240, the apparatus for measuring a bio-signal may operate the second optical sensor in the light source mode to emit light to the object of interest.

In operation 1250, the apparatus for measuring a bio-signal may operate the first optical sensor in the photodetector mode to receive light reflected or scattered from the object of interest and acquire second optical absorption information.

In operation 1260, the apparatus for measuring a bio-signal may compare the first optical absorption information and the second optical absorption information and determine the contact state between the object of interest and the optical sensor array on the basis of the comparison result. For example, when a difference between the first optical absorption information and the second optical absorption information is lower than or equal to a predetermined threshold, the apparatus may determine that the optical sensor array is in good contact with the object of interest. When the difference between the first optical absorption information and the second optical absorption information is greater than the predetermined threshold, the apparatus may determine that the optical sensor array is in poor contact with the object of interest.

The current embodiments can be implemented as computer-readable instructions or code in a non-transitory computer-readable storage medium. The computer-readable storage medium includes all types of storage media in which computer-readable data are stored. Examples of the computer-readable storage medium include a ROM, a RAM, a compact disc ROM (CD-ROM), a magnetic tape, a floppy disk, and an optical data storage. In addition, the computer-readable storage medium may be distributed among computer systems over a network, in which computer-readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An optical sensor comprising:
a photodetector;
a light source disposed on the photodetector;
a photodetector electrode on which the photodetector is disposed;
a common electrode interposed between the photodetector and the light source;
a light source electrode disposed on the light source;
a power source;
a first switch configured to connect the light source electrode and the common electrode to the power source, in a light source mode; and
a second switch configured to connect the photodetector electrode and the common electrode to the power source, in a photodetector mode,
wherein the optical sensor is configured to operate as one of the light source in the light source mode and the photodetector in the photodetector mode, based on a control signal that switches between the light source mode and the photodetector mode.

2. The optical sensor of claim 1, wherein the common electrode is configured to reflect light that is emitted from a light emitting layer of the light source toward the photodetector.

3. The optical sensor of claim 1, wherein the common electrode comprises one among conductive materials including Al, Ag, Pt, Pd, Au, Rh, Al alloy, Ag alloy, Pt alloy, Pd alloy, Au alloy, and Rh alloy.

4. The optical sensor of claim 1, wherein the control signal comprises mode selection information indicating one among the light source mode and the photodetector mode that is selected, and mode duration information of the selected one among the light source mode and the photodetector mode.

5. The optical sensor of claim 4, wherein the control signal is pulse-shaped.

6. An optical sensor array comprising:
a plurality of optical sensors,
wherein each of the plurality of optical sensors includes:
a photodetector; and
a light source disposed on the photodetector;
a photodetector electrode on which the photodetector is disposed;
a common electrode interposed between the photodetector and the light source;
a light source electrode disposed on the light source;
a power source;
a first switch configured to connect the light source electrode and the common electrode to the power source, in a light source mode; and
a second switch configured to connect the photodetector electrode and the common electrode to the power source, in a photodetector mode, and
wherein each of the plurality of optical sensors is configured to operate as one of the light source in the light source mode and the photodetector in the photodetector mode, based on a control signal that switches between the light source mode and the photodetector mode.

7. The optical sensor array of claim 6, wherein the optical sensor array is a square array or a hexagonal array.

8. An apparatus for measuring a bio-signal, the apparatus comprising:
an optical sensor array comprising a plurality of optical sensors, each of the plurality of optical sensors comprising:
a photodetector; and
a light source disposed on the photodetector;
a photodetector electrode on which the photodetector is disposed;
a common electrode interposed between the photodetector and the light source;
a light source electrode disposed on the light source;
a power source;
a first switch configured to connect the light source electrode and the common electrode to the power source, in a light source mode; and
a second switch configured to connect the photodetector electrode and the common electrode to the power source, in a photodetector mode,
wherein each of the plurality of optical sensors is configured to operate as one of the light source in the light source mode and the photodetector in the photodetector mode, based on a control signal that switches connection between the first switch and the second switch; and
a processor configured to control one among the plurality of optical sensors to operate in the light source mode, and control at least two among the plurality of optical sensors to operate in the photodetector mode, to acquire optical absorption information of optical pathlengths with respect to an object of interest.

9. The apparatus of claim 8, wherein the processor is further configured to control the one among the plurality of optical sensors to emit first light to the object of interest, and control the at least two among the plurality of optical sensors to receive second light that is reflected or scattered from the object of interest to which the first light is emitted, to acquire the optical absorption information of the optical pathlengths.

10. The apparatus of claim 8, wherein the processor is further configured to estimate bio-information of the object of interest, based on the acquired optical absorption information of the optical pathlengths.

11. The apparatus of claim 10, wherein the bio-information comprises any one or any combination of triglyceride, blood glucose, cholesterol, protein, and uric acid.

12. The apparatus of claim 8, wherein the processor is further configured to determine a contact state between the optical sensor array and the object of interest, using a pair of the plurality of optical sensors.

13. The apparatus of claim 12, wherein the processor is further configured to:
control a first one of the pair of the plurality of optical sensors to operate in the light source mode, and control a second one of the pair of the plurality of optical sensors to operate in the photodetector mode, to acquire first optical absorption information;
control the second one of the pair of the plurality of optical sensors to operate in the light source mode, and control the first one of the pair of the plurality of optical sensors to operate in the photodetector mode, to acquire second optical absorption information; and
compare the acquired first optical absorption information and the acquired second optical absorption information, to determine the contact state between the optical sensor array and the object of interest.

14. The apparatus of claim 12, wherein the processor is further configured to, based on the contact state between the optical sensor array and the object of interest being determined to be poor, control to provide a warning message to a user.

15. The apparatus of claim 8, wherein the common electrode is configured to reflect light that is emitted from a light emitting layer of the light source toward the photodetector.

16. The apparatus of claim 8, wherein the common electrode comprises one among conductive materials including Al, Ag, Pt, Pd, Au, Rh, Al alloy, Ag alloy, Pt alloy, Pd alloy, Au alloy, and Rh alloy.

17. The apparatus of claim 8, wherein the optical sensor array is a square array or a hexagonal array.

18. A method of measuring a bio-signal, using an optical sensor array that comprises a plurality optical sensors, each of the plurality of optical sensors comprising a photodetector and a light source disposed on the photodetector, a photodetector electrode on which the photodetector is disposed, a common electrode interposed between the photodetector and the light source, a light source electrode disposed on the light source, and a power source, each of the plurality of optical sensors operating as one of the light source in a light source mode and the photodetector in a photodetector mode, based on a control signal, the method comprising:
    controlling one among the plurality of optical sensors to operate in the light source mode by connecting the light source electrode and the common electrode to the power source by a first switch so that the one among the plurality of optical sensors emits first light to an object of interest; and
    controlling at least two among the plurality of optical sensors to operate in the photodetector mode based on connecting the photodetector electrode and the common electrode to the power source by a second switch so that the at least two among the plurality of optical sensors receive second light that is reflected or scattered from the object of interest to which the first light is emitted, to acquire optical absorption information of optical pathlengths with respect to the object of interest.

19. The method of claim 18, further comprising estimating bio-information of the object of interest, based on the acquired optical absorption information of the optical pathlengths.

20. The method of claim 19, wherein the bio-information comprises any one or any combination of triglyceride, blood glucose, cholesterol, protein, and uric acid.

21. The method of claim 18, further comprising determining a contact state between the optical sensor array and the object of interest, using a pair of the plurality of optical sensors.

22. The method of claim 21, further comprising:
    controlling a first one of the pair of the plurality of optical sensors to operate in the light source mode, and controlling a second one of the pair of the plurality of optical sensors to operate in the photodetector mode, to acquire first optical absorption information; and
    controlling the second one of the pair of the plurality of optical sensors to operate in the light source mode, and controlling the first one of the pair of the plurality of optical sensors to operate in the photodetector mode, to acquire second optical absorption information,
    wherein the determining the contact state between the optical sensor array and the object of interest comprises comparing the acquired first optical absorption information and the acquired second optical absorption information.

23. The method of claim 21, further comprising, based on the contact state between the optical sensor array and the object of interest being determined to be poor, controlling to provide a warning message to a user.

24. A mobile device comprising:
    an optical sensor array comprising a plurality of optical sensors, each of the plurality of optical sensors comprising:
        a photodetector; and
        a light source disposed on the photodetector;
        a photodetector electrode on which the photodetector is disposed;
        a common electrode interposed between the photodetector and the light source;
        a light source electrode disposed on the light source;
        a power source;
        a first switch configured to connect the light source electrode and the common electrode to the power source, in a light source mode; and
        a second switch configured to connect the photodetector electrode and the common electrode to the power source, in a photodetector mode; and
    a processor configured to control one among the plurality of optical sensors to emit first light to an object of interest based on connecting the first switch, and control at least two among the plurality of optical sensors to receive second light that is reflected or scattered from the object of interest to which the first light is emitted based on connecting the second switch, to acquire optical absorption information of optical pathlengths with respect to the object of interest.

25. The mobile device of claim 24, wherein the processor is further configured to:
    determine a contact state between the optical sensor array and the object of interest;
    based on the contact state between the optical sensor array and the object of interest being determined to be poor, control to provide a warning message to a user; and
    based on the contact state between the optical sensor array and the object of interest being determined to be good, control the one among the plurality of optical sensors to emit the first light to the object of interest, and control the at least two among the plurality of optical sensors to receive the second light that is reflected or scattered from the object of interest to which the first light is emitted, to acquire the optical absorption information of the optical pathlengths.

* * * * *